United States Patent
Mondello (10) Patent No.: US 7,355,703 B2
(45) Date of Patent: Apr. 8, 2008

(54) RAMAN-ACTIVE LATERAL FLOW DEVICE AND METHODS OF DETECTION AND MAKING

(75) Inventor: Frank John Mondello, Niskayuna, NY (US)

(73) Assignee: GE Homeland Protection, Inc., Newark, CA (US)

( * ) Notice: Subject to any disclaimer, the term of this patent is extended or adjusted under 35 U.S.C. 154(b) by 102 days.

(21) Appl. No.: 11/257,164

(22) Filed: Oct. 24, 2005

(65) Prior Publication Data

US 2007/0058165 A1 Mar. 15, 2007

Related U.S. Application Data

(63) Continuation-in-part of application No. 11/223,353, filed on Sep. 9, 2005.

(51) Int. Cl.
*G01J 3/44* (2006.01)
(52) U.S. Cl. ..................................... 356/301
(58) Field of Classification Search ................ 356/301; 436/518
See application file for complete search history.

(56) References Cited

U.S. PATENT DOCUMENTS

| | | |
|---|---|---|
| 6,514,767 B1 | 2/2003 | Natan |
| 6,573,108 B1 * | 6/2003 | Hardman et al. ........... 436/518 |
| 6,579,721 B1 | 6/2003 | Natan |
| 2003/0166297 A1 | 9/2003 | Natan |
| 2005/0089901 A1 * | 4/2005 | Porter et al. .................... 435/6 |
| 2005/0130163 A1 | 6/2005 | Smith et al. |

FOREIGN PATENT DOCUMENTS

WO WO2006073439 A2 7/2006

OTHER PUBLICATIONS

J. Ni, et al., "Immunoassay readout method using extrinstic raman labels adsorbed on immunogold colloids", Anal. Chem. 71, 4903-4908, 1999.
S. P. Mulvaney, et al., "Glass-coated, analyte tagged nanoparticles: A new tagging system based on detection with surface-enhanced raman scattering", Langmuir, 19, 4784-4790, 2003.
D. S. Grubisha, et al., "Femtomolar detection of prostate-specific antigen: An immunoassay based on surface-enhanced ramen scattering and immunogold labels", Anal. Chem., 75 (21) 5936-43, 2003.

* cited by examiner

*Primary Examiner*—Gregory J. Toatley, Jr.
*Assistant Examiner*—Bryan J Giglio
(74) *Attorney, Agent, or Firm*—William E. Powell, III; Curtis B. Brueske (57) ABSTRACT

A lateral flow device is disclosed. The lateral flow device includes a substrate having a flow path and a detection zone disposed along the flow path. The detection zone includes an immobilized target-binding moiety directed against a target of a Raman-active complex. A portion of the detection zone has a dimension that is less than another dimension of the lateral flow device upflow from the detection zone or a first region of the detection zone has a chemical difference from a second region of the detection zone. Also disclosed are methods of conducting a lateral flow assay and methods of making a lateral flow device.

53 Claims, 6 Drawing Sheets

RAMAN-ACTIVE LATERAL FLOW DEVICE AND METHODS OF DETECTION AND MAKING

CROSS REFERENCE TO RELATED APPLICATIONS

This application is a continuation-in-part of U.S. patent application Ser. No. 11/223,353, filed Sep. 9, 2005, which is hereby incorporated by reference.

BACKGROUND

The invention includes embodiments that may relate to Raman-active lateral flow devices, assays, and/or methods.

DESCRIPTION OF RELATED ART

Figure 1:
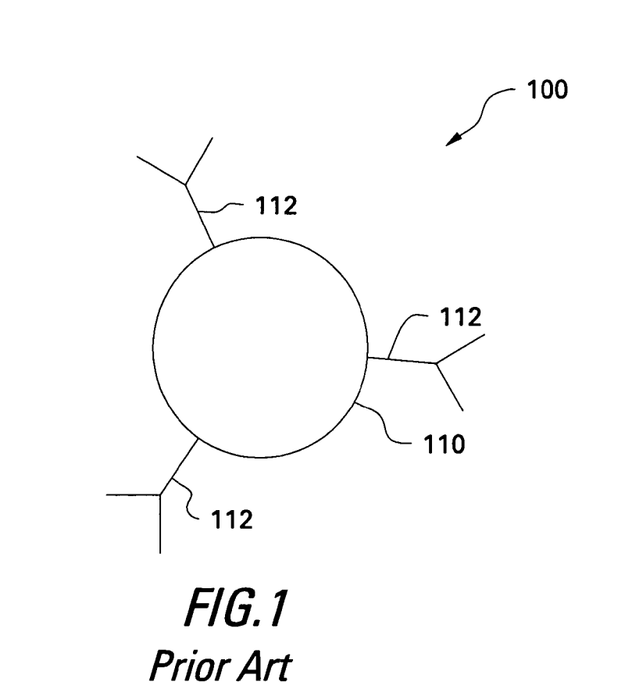
FIG. 1 is a schematic representation of a known unattached Raman-active tag.
Figure 2:
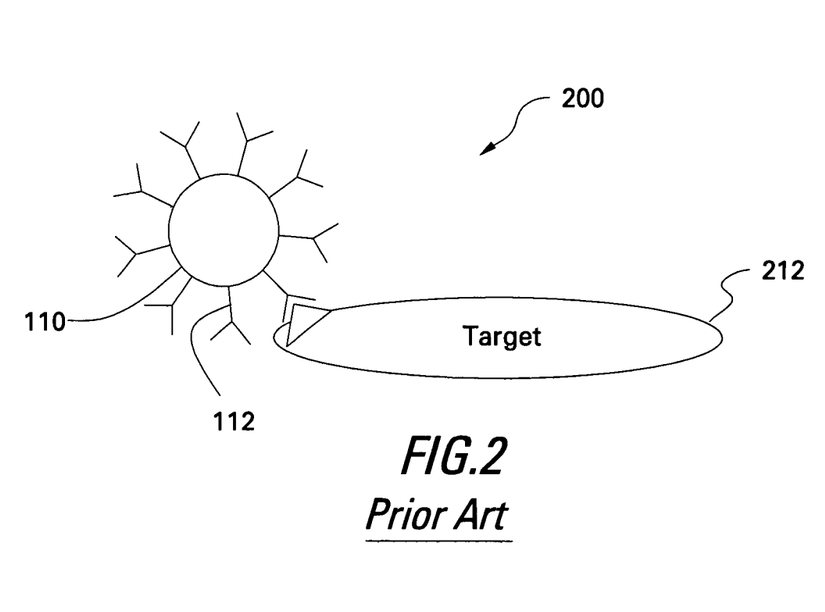
FIG. 2 is a schematic representation of a known Raman-active complex.

Some assays or methods for detecting the presence of pathogenic organisms or other materials are known. Also known are Raman and surface enhanced Raman-active tags 100. FIG. 1 is a schematic representation of a Raman-active tag 100 that includes one or more target-binding moieties 112 attached to a Raman-active particle 110. The target-binding moiety 112 on the Raman-active tag 100 can attach to one or more targets 212 to form a Raman-active complex 200 as shown in FIG. 2.

A need may exist for methods and systems for detecting the presence of pathogenic organisms or other materials that differ from those currently available. It may be desirable to have a device, system, or method that detects organisms or materials that differs from those currently available. It may be desirable to have a device, system or method that quantifies or identifies organisms or materials that differs from those currently available.

BRIEF DESCRIPTION

The purpose of embodiments of the invention will be set forth and apparent from the description that follows, as well as will be learned by practice of the embodiments of the invention.

An embodiment provides a lateral flow device. The lateral flow device includes a substrate having a flow path and a detection zone disposed along the flow path. The detection zone includes an immobilized target-binding moiety directed against a target of a Raman-active complex. A portion of the detection zone has a dimension that is less than another dimension of the lateral flow device upflow from the detection zone, or a first region of the detection zone has a chemical difference from a second region of the detection zone.

Another embodiment provides a detection system. The detection system includes a lateral flow device and a Raman spectrometer. The lateral flow device includes a substrate having a flow path and a detection zone disposed along the flow path. The detection zone includes an immobilized target-binding moiety directed against a target of a Raman-active complex. A portion of the detection zone has a dimension that is less than another dimension of the lateral flow device upflow from the detection zone, or a first region of the detection zone has a chemical difference from a second region of the detection zone. The Raman spectrometer is capable of detecting a Raman-active complex at the detection zone.

Another embodiment provides a method of conducting a lateral flow assay. The method includes i) defining a flow path having a detection zone; ii) flowing a sample down the flow path; and iii) immobilizing a Raman-active complex, if present, at the detection zone. The sample includes a Raman-active complex or a Raman-active tag. A portion of the detection zone has a dimension that is less than another dimension of the lateral flow device upflow from the detection zone, or a first region of the detection zone has a chemical difference from a second region of the detection zone.

Another embodiment provides a method of conducting a lateral flow assay. The method includes concentrating a Raman-active complex, if present, at a portion of a detection zone of a lateral flow assay.

Another embodiment provides a method of making the lateral flow device. The method includes providing a lateral flow device with a detection zone. A portion of the detection zone has a dimension that is less than another dimension of the lateral flow device upflow from the detection zone or a first region of the detection zone has a chemical difference from a second region of the detection zone.

The accompanying figures, which are incorporated in and constitute part of this specification, are included to illustrate and provide a further understanding of the method and system of the invention. Together with the description, the drawings serve to explain the principles of the invention.

BRIEF DESCRIPTION OF THE DRAWINGS

FIG. 7A is a background SERS (Surface Enhanced Raman Spectroscopy) spectrum obtained from a lateral flow assay between the detection zone and the control zone in accordance with an embodiment of the invention;

FIG. 7B is a SERS spectrum from a detection zone of a lateral flow assay in the presence of *botulinum* toxoid; and FIG. 7C is a SERS spectrum from a detection zone of a lateral flow assay in accordance with an embodiment of the invention in the presence of *botulinum* toxoid.

DETAILED DESCRIPTION

In at least some embodiments, the concentration of a detectable Raman-active complex may be relatively increased to aid in the detection of the target. Accordingly, some methods, devices and systems may facilitate or increase the Raman-active complex concentration, and therefore the ease of detection, of the target. Reference will now be made in detail to exemplary embodiments of the invention, which are illustrated in the accompanying figures and examples. Referring to the drawings in general, it will be understood that the illustrations are for the purpose of describing a particular embodiment of the invention and are not intended to limit the invention thereto.

Whenever a particular embodiment of the invention is said to comprise or consist of at least one element of a group and combinations thereof, it is understood that the embodiment may comprise or consist of any of the elements of the group, either individually or in combination with any of the other elements of that group. Furthermore, when any variable occurs more than one time in any constituent or in formula, its definition on each occurrence is independent of its definition at every other occurrence. Also, combinations of substituents and/or variables are permissible only if such combinations result in stable systems, methods, and Raman-active complexes.

Lateral flow devices and methods for detecting the presence of a target pathogenic organism or other material using Raman-active tags are disclosed.

Figure 3A:
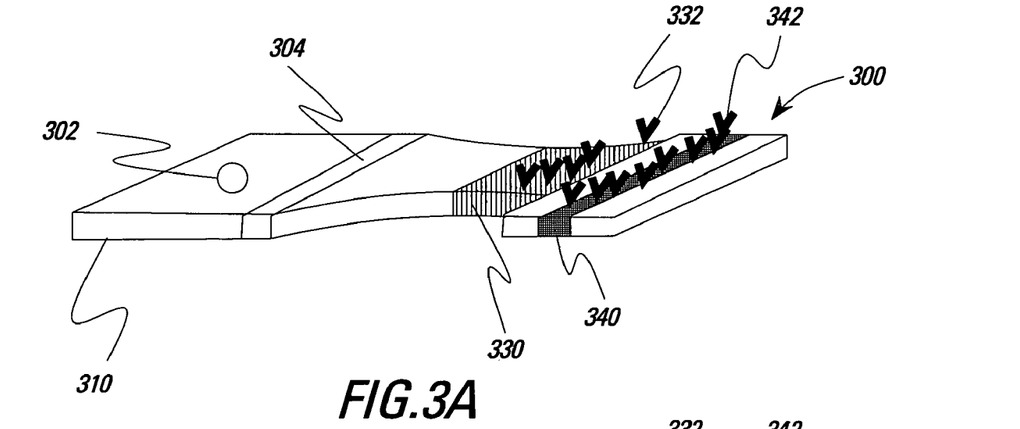
FIG. 3A-3C are schematic representations of a lateral flow device in accordance with an embodiment of the invention.
Figure 3B:
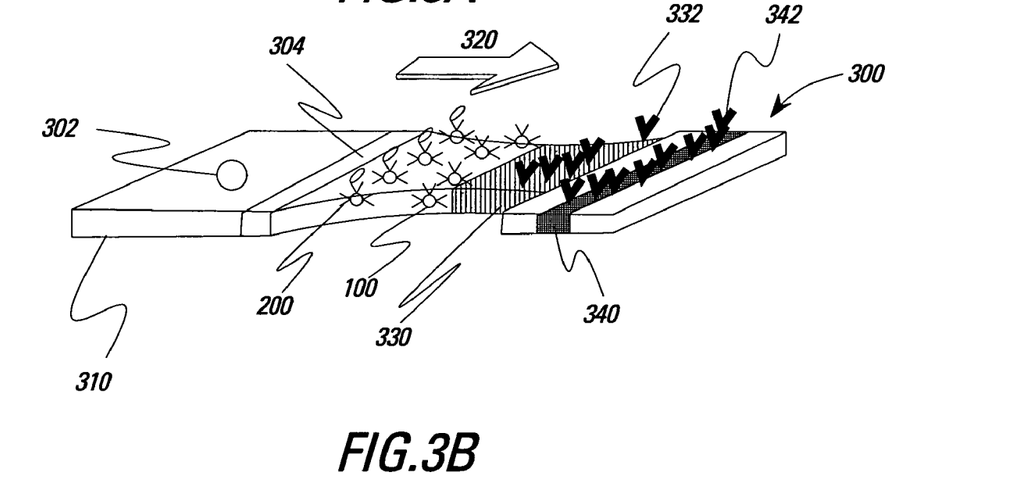
Figure 3C:
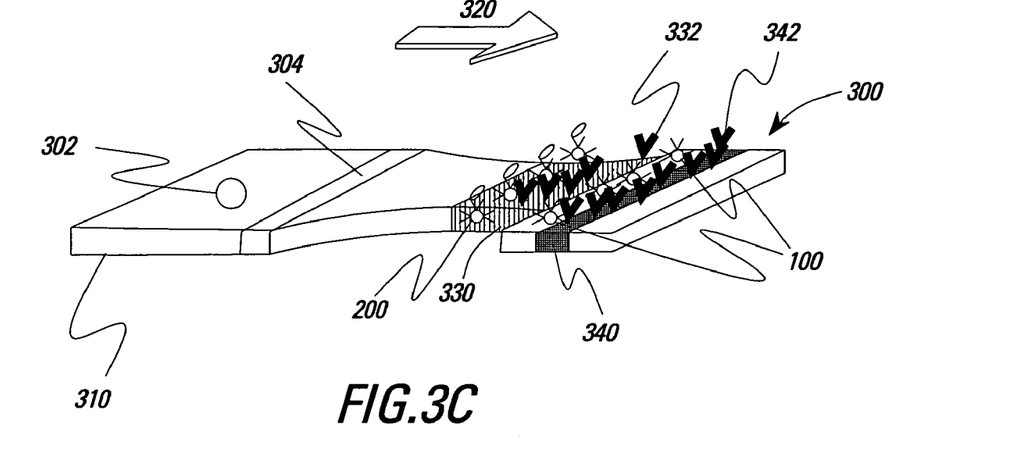

With reference to FIG. 3, there is shown one embodiment of a lateral flow device 300. The lateral flow device 300 may have a predetermined shape and one or more predetermined dimensions, such as depth, width, and length. The lateral flow device 300 includes a substrate 310 having one or more flow paths 320 and one or more detection zones 330. The detection zone 330 is disposed along the flow path 320. The detection zone 330 includes one or more immobilized target-binding moieties 332 directed against a target of a Raman-active complex. In a particular embodiment, the lateral flow device may have one or more control zones 340. The control zone 340 is disposed along the flow path 320 downflow from the detection zone 330 and includes one or more immobilized particle-binding-moieties 342 directed against a Raman-active tag. Downflow from the detection zone 330 means towards the direction of the flow path as indicated by the arrow. The lateral flow device 300 may also include one or more sample zones 302 for depositing a sample and one or more contact zones 304.

Raman-Active Tag and Raman-Active Complex

Unless noted otherwise, the word "Raman" and "Raman-active" includes Raman, surface-enhanced Raman, resonance Raman, and surface-enhanced resonance Raman spectroscopies.

In one embodiment, the Raman-active tag is immuno-functionalized. Immuno-functionalized Raman-active tags are capable of detecting the presence of one or more targets, such as pathogenic organisms or other materials. Immuno-functionalized Raman-active tags include Raman-active tags having one or more target-binding moieties, such as an antibody. The target-binding moiety can attach to the Raman-active tag, and to a target to which the target-binding moiety is directed, to form a Raman-active complex. Attached includes the target-binding moiety covalently or non-covalently connected to a target.

The Raman-Active Tag or Raman-Active Complex

The Raman-active tag may include one or more Raman-active particles. The Raman-active particles may be selected to have a predetermined size, shape and material composition based on the end-use. In one embodiment, the Raman-active particle includes a core, a coating, and a Raman-active analyte. The Raman-active particle may include one or more cores, one or more coatings, and one or more analytes. In one embodiment, the analyte is at least partially within the coating and the coating at least partially covers the core. In a particular embodiment, the coating covers the core.

In one embodiment, the core has a metallic surface. The core may include a metal such as, but not limited to, Au, Ag, Cu, Ni, Pd, Pt, Na, Al, and Cr, either individually or in a combination of two or more thereof. The core may include an inorganic or an organic material, provided the surface of the core is metallic. In a particular embodiment, the core includes gold (Au).

The shape of the core may be selected based on the end-use. For example, the core may be in the shape of a sphere, fiber, plate, cube, tripod, pyramid, rod, tetrapod, or any non-spherical object. In one embodiment, the core is spherical.

The size of the core also may be predetermined based on its composition and intended use. In one embodiment, the cores have an average diameter in a range from about 1 nanometer (nm) to about 500 nm. In another embodiment, the cores have an average diameter less than about 100 nm. In yet another embodiment, the cores have an average diameter in a range from about 12 nm to about 100 nm. The particle size distribution may be selected with reference to the application, but in one embodiment may be about 1 nm.

In one embodiment, the coating includes stabilizer that may reduce or eliminate Raman-active particle aggregation. The coating stabilizes the Raman-active particle in one way by inhibiting aggregation of Raman-active particles. The coating is sufficiently thick to stabilize the Raman-active particle. In one embodiment, the coating has a thickness in a range from about 1 nm to about 500 nm. In another embodiment, the coating has a thickness in a range from about 5 nm to about 30 nm.

In one embodiment, the coating includes an elemental oxide. In a particular embodiment, the element in the elemental oxide includes silicon. The percentage of silicon may depend on one or more factors. Such factors may include the intended use of the Raman-active particle, the composition of the core, the degree to which the coating is to be functionalized, the desired density of the coating for a given application, the desired melting point for the coating, the identity of any other materials which constitute the coating, and the technique by which the Raman-active particle is to be prepared. In one embodiment, the element in the elemental oxide of the coating includes at least about 50-mole % silicon. In another embodiment, the element in the elemental oxide of the coating includes at least about 70-mole %. Yet, in another embodiment, the element in the elemental oxide of the coating includes substantially silicon.

In yet another embodiment, the coating includes a composite. A composite coating may include oxides of one or more elements such as, but not limited to, Si, B, Al, Ga, In, Sc, Y, La, Ti, Zr, Hf, V, Nb, Ta, Cr, Mn, Fe, Co, Ni, Li, Na, K, Rb, Cs, Be, Mg, Ca, Sr, Ba, Zn, Cd, Ge, Sn, and Pb. Furthermore, the coating may include multilayer coatings. Each of the coating layers in the multilayer coating individually may include different coating compositions, such as 50-mole % silicon oxide in one coating layer and a composite coating in another coating layer.

The Raman-active particle includes one or more Raman-active analytes. In one embodiment, the Raman-active analyte is a molecule that exhibits Raman scattering when in the vicinity of a metallic core or a metallic surface of a core. Examples of Raman-active analytes include, but are not limited to, 4-mercaptopyridine, 2-mercaptopyridine (MP), trans-bis(pyridyl)ethylene (BPE), naphthalene thiol (NT), 4,4'-dipyridyl (DPY), quinoline thiol (QSH), and mercaptobenzoic acid, either individually or any combination thereof. In a particular embodiment, the Raman-active analyte includes trans-bis(pyridyl)ethylene and or quinoline thiol.

In one embodiment, the Raman-active analyte is at least partially within the coating. The Raman-active analyte can be at least partially within the coating in various orientations, such as, but not limited to, dispersed within the coating, within and around the coating, or embedded within the coating. Furthermore, a plurality of analytes may be within the coating. The plurality of analytes may be within the coating at a plurality of sites or at a single site. It should be appreciated that each of the analytes may be within the coating by a different mode, such as dispersed within the coating, around the coating, or embedded within the coating.

The Raman-active particle may include one core within a coating or multiple cores within a coating. The multiple cores are non-aggregated or closer together. There may be particular advantages associated with Raman-active particles that have one core within a coating or multiple cores within a coating. The selection as to how many cores should be contained within a coating may depend on the particular application for which the Raman-active particles are being used. Adjusting process conditions may be effective in obtaining Raman-active particles with a single core contained in the coating. For example, the coating may also stabilize a core against aggregating with another core.

The Raman-active particle may vary in shape and size. In one embodiment, the Raman-active particles are substantially spherical and have an average diameter in a range less than about 1000 nm. In a particular embodiment, the Raman-active particle has an average diameter less than about 100 nm In one embodiment, the Raman-active particle includes one or more linkers. The linker binds to the core and interacts with the coating. The linker allows or facilitates the coating to attach to the core. The linker may be a molecule having a functional group. The functional group can bind to the metal surface of the core and bind to the coating. An example of a linker is alkoxysilanes. Examples of alkoxysilanes include trialkoxysilanes. Trialkoxysilane linkers may be used to deposit coatings comprising silica. Suitable trialkoxysilane linkers include, but are not limited to, aminopropyl trimethoxysilane (APTMS), aminopropyl triethoxysilane, mercaptopropyl trimethoxysilane, mercaptopropyl triethoxysilane, hydroxypropyl trimethoxysilane, and hydroxypropyl triethoxysilane, either individually or in any combinations thereof.

When more than one analyte, coating, linker, and core are present, the definition on each occurrence is independent of the definition at every other occurrence. Also, combinations of an analyte, coating, linker, and core are permissible if such combinations result in stable Raman-active particles. Also, methods in combining an analyte, coating, linker, and core are permissible if such combinations result in stable Raman-active particles.

Targets and Target-Binding Moieties

Target-binding moieties are capable of attaching to the target, directly or indirectly. The lateral flow device is not limited by how the target-binding moieties attach to the target. Examples of attaching include, but are not restricted to, electrostatically, chemically, and physically. Attached means at least partially attached such that the target-binding moiety at least partially attaches to the substrate. "Attached" may be used in combination with a term, and may include a number or amount of movement or non-attachment while still being considered attached. Examples of target-binding moieties include, but are not limited to, antibodies, aptamers, polypeptides, peptides, nucleic acids, avidin, streptavidin, and derivatives of avidin and streptavidin, either individually or in any combination thereof. The Raman-active tag may include one target-binding moiety or a plurality of target-binding moieties. The plurality of target-binding moieties may all be of the same kind of target-binding moieties or different kinds of target-binding moieties capable of attaching to different types of target.

A target may be attached to one Raman-active complex or a plurality of Raman-active complexes. Targets include living or non-living targets. Examples of targets include, but are not limited to, prokaryotic cells, eukaryotic cells, bacteria, viruses, proteins, polypeptides, toxins, liposomes, beads, ligands, amino acids, and nucleic acids, either individually or in any combinations thereof. The target also includes extracts of the above, living or non-living targets.

Examples of prokaryotic cells include, but are not limited to, bacteria and extracts thereof. Examples of eukaryotic cells include, but are not limited to, yeast cells, animal cells, and tissues. Examples of toxins include, but are not limited to, anthrax. Examples of beads include, but are not limited to, latex, polystyrene, silica and plastic. In one embodiment, the beads may be small spherical shaped particles.

The term "peptide" refers to oligomers or polymers of any length wherein the constituent monomers are alpha amino acids linked through amide bonds, and encompasses amino acid dimers as well as polypeptides, peptide fragments, peptide analogs, naturally occurring proteins, mutated, variant or chemically modified proteins, fusion proteins, and the like. The amino acids of the peptide molecules may be any of the twenty conventional amino acids, stereoisomers (e.g., D-amino acids) of the conventional amino acids, structural variants of the conventional amino acids, e.g., iso-valine, or non-naturally occurring amino acids such as $\alpha,\alpha$-disubstituted amino acids, N-alkyl amino acids, $\beta$-alanine, naphthylalanine, 3-pyridylalanine, 4-hydroxyproline, O-phosphoserine, N-acetylserine, N-formylmethionine, 3-methylhistidine, 5-hydroxylysine, and nor-leucine. In addition, the term "peptide" encompasses peptides with modification such as posttranslational modifications. Examples of posttranslational modifications include, but are not limited to, glycosylations, acetylations, phosphorylations, and the like.

The term "oligonucleotide" is used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. The term also includes modifications, such as by methylation and/or by capping, and unmodified forms of the oligonucleotide. More particularly, the term includes polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholine (commercially available from the Anti-Virals, Inc., Corvallis, Oreg., as NEUGENE) polymers, and other synthetic sequence-specific nucleic acid polymers, providing that the polymers contain nucleobases in a configuration that allows for base pairing and base stacking, such as is found in DNA and RNA.

There is no intended distinction in length between the terms "polynucleotide", "oligonucleotide", "nucleic acid" and "nucleic acid molecule", and these terms refer only to the primary structure of the molecule. The terms "nucleoside" and "nucleotide" also include those moieties that contain not only the known purine and pyrimidine bases, but also other heterocyclic bases, which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

Furthermore, modifications to nucleotidic units include rearranging, appending, substituting for or otherwise altering functional groups on the purine or pyrimidine base that form hydrogen bonds to a respective complementary pyrimidine or purine. The resultant modified nucleotidic unit optionally may form a base pair with other such modified nucleotidic units but not with A, T, C, G or U. Basic sites may be incorporated which do not prevent the function of the polynucleotide. Some or all of the residues in the polynucleotide can optionally be modified in one or more ways.

The term "antibody" as used herein includes antibodies obtained from both polyclonal and monoclonal preparations, as well as hybrid (chimeric) antibody molecules; F(ab')2 and F(ab) fragments; Fv molecules (noncovalent heterodimers); single-chain Fv molecules (sFv); dimeric and trimeric antibody fragment constructs; humanized antibody molecules; and any functional fragments obtained from such molecules, wherein such fragments retain specific-binding properties of the parent antibody molecule.

Substrate:

The substrate may vary in size, shape, and material. In one embodiment, the substrate includes nitrocellulose membrane. Other membrane types include cellulose acetate, glass fiber, polyethersulfone, nylon, or other polymers, either individually or in combinations thereof. In one embodiment, the substrate may have dimensions from about 5 mm to about 580 mm in length, from about 1 mm to about 150 mm in width, and from about 0.0001 mm to about 5 mm thick. In another embodiment, the substrate has a dimension in a range of 58 mm length×5 mm width×0.5 mm thickness.

Flow Path

A flow path 320 is the direction of movement of a Raman-active tag or Raman-active complex, as shown by the movement of the arrow from FIG. 3A to FIG. 3B to FIG. 3C. The sample containing the suspected target and the Raman-active tags or Raman-active complex may be drawn by capillary action from the point of deposit (such as the sample zone 302 in FIG. 3A) across the substrate to another location, (such as the detection zone or contact zone as shown in FIG. 3B and FIG. 3C) as shown by the movement of the flow path 320 arrow. In one embodiment, the sample is a liquid, and the movement is assisted by an absorbent pad contacting the substrate. The flow paths of a plurality of Raman-active tags or complexes can be shared, or similar or be unique.

Sample Zone

The lateral flow device is not limited by how and when the Raman-active tags and the target come in contact with each other. In one embodiment, the sample is deposited in or onto the sample zone 302, which is upflow from the detection zone, as shown in FIG. 3A. Upflow from the detection zone 330 mean away from the direction of the flow path 320 as indicated by the arrow.

Contact Zone

In one embodiment, the Raman-active tag and the target come in contact at the contact zone 304, such as when a sample containing the Raman-active tag and another sample containing the suspected target are deposited sequentially or simultaneously at the contact zone. The contact zone is located upflow from the detection zone. In one embodiment, the Raman-active tags are predispositioned on a conjugate pad, which may be placed on the contact zone or be the contact zone.

In another embodiment, a Raman-active tag and target are already in contact with each other before the contact zone, such as when a sample includes the Raman-active tag and the suspected target and is deposited simultaneously.

Detection Zone

The detection zone may be of varying material, shape, and dimension, such as length, width, and height. In one embodiment, a portion of the detection zone includes a physical difference and or a chemical difference.

Figure 4A:
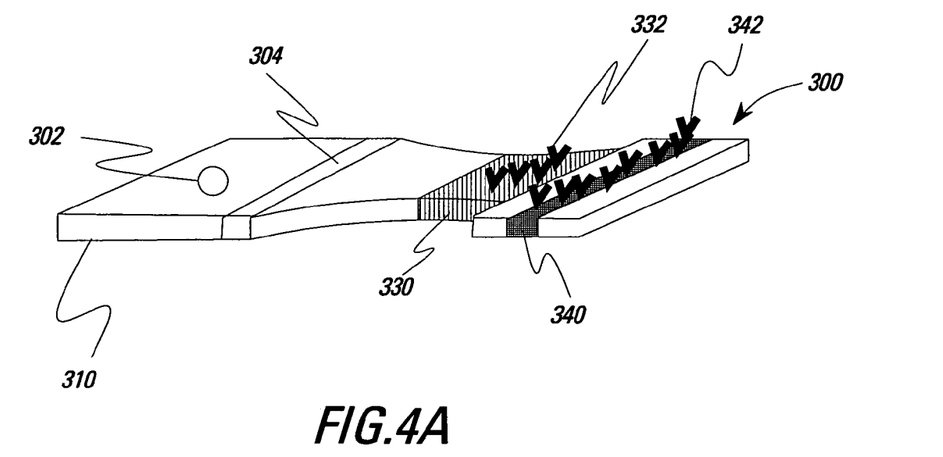
FIG. 4A-4C are schematic representations of a lateral flow device in accordance with an embodiment of the invention.
Figure 4B:
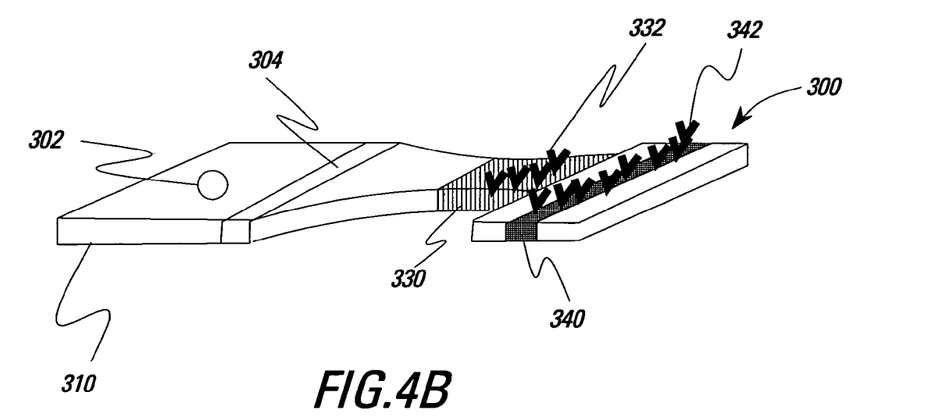
Figure 4C:
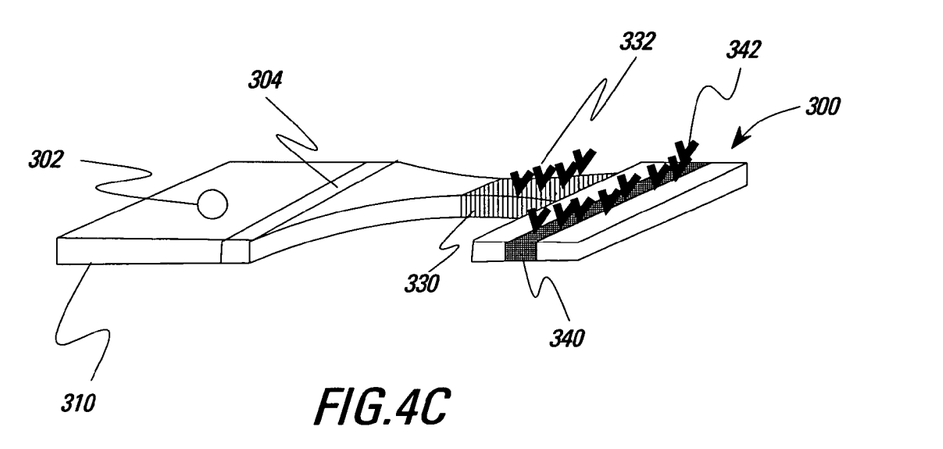

In one embodiment, the detection zone includes a physical difference. In a particular embodiment, a portion of the detection zone has one or more dimensions that are less than another dimension of the lateral flow device upflow from the detection zone. Physically different includes tapering, narrowing, decreasing, or otherwise modifying. Approximating language, as used herein throughout the specification and claims, may be applied to modify any quantitative or qualitative representation that could permissibly vary without resulting in a change in the basic function to which it is related. Accordingly, a value modified by a term such as "about" is not to be limited to the precise value specified, and may include values that differ from the specified value. In at least some instances, the approximating language may correspond to the precision of an instrument for measuring the value. Similarly, "tapering or narrowing or decreasing" may be used in combination with a term, and may include an insubstantial number or trace amount of a physical difference or modification while still being considered different or modified. For example, in a particular embodiment, at least a portion of the detection zone has one or more dimensions that is at least 20% less than another dimension of the lateral flow device upflow from the detection zone, as shown in FIG. 4A. In a more particular embodiment, a dimension of the detection zone 330 is at least 50% less than another dimension of the lateral flow device upflow from the detection zone, as shown in FIG. 4B. In yet a more particular embodiment, a dimension of the detection zone 330 is at least 75% less than another dimension of the lateral flow device upflow from the detection zone, as shown in FIG. 4C. In other embodiments, the dimension of the detection zone 330 may also be 20%-30%, 30%-40%, 40%-50%, 60%-70%, or 70%-80% less than another dimension of the lateral flow device upflow from the detection zone. The dimension of the detection zone may be decreased in a continuous tapered gradual manner or in a sharp incremental manner. The detection zone may be decreased from multiple sides of the detection zone, as shown in FIG. 4A-C, or decreased from one side of the detection zone.

The dimension of the detection zone 330 that is physically different may be any dimension such as length, width, or height. In a particular embodiment, at least a portion of the width of the detection zone 330 is at least 20% less than another dimension of the lateral flow device upflow from the detection zone, as shown in FIG. 4A. In a more particular embodiment, at least a portion of the width of the detection zone 330 is at least 50% less than another dimension of the lateral flow device upflow from the detection zone, as shown in FIG. 4B. In yet a more particular embodiment, at least a portion of the width of the detection zone 330 is at least 75% less than another dimension of the lateral flow device upflow from the detection zone, as shown in FIG. 4C. In one embodiment, a dimension of the detection zone 330 is less than another dimension of the lateral flow device upflow from the detection zone and less than another dimension of the lateral flow device downflow from the detection zone.

Figure 5A:
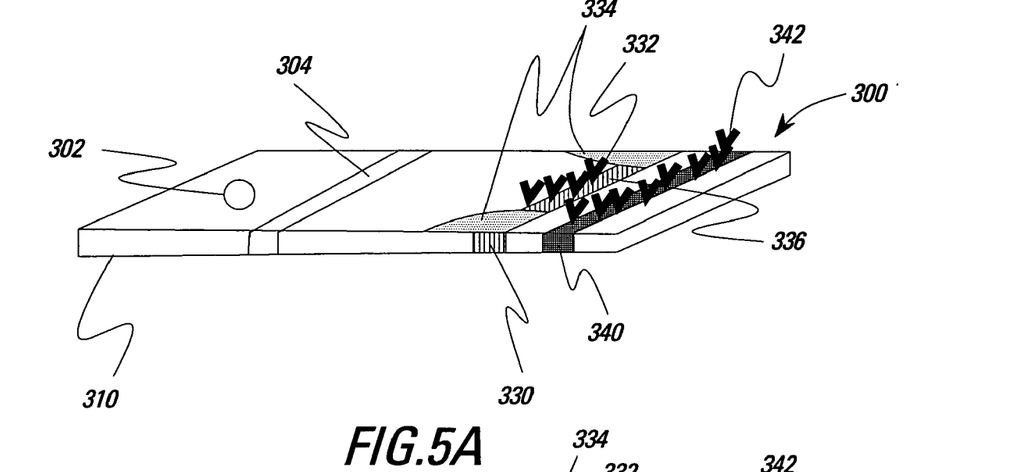
FIG. 5A-5C are schematic representations of a lateral flow device in accordance with an embodiment of the invention.
Figure 5B:
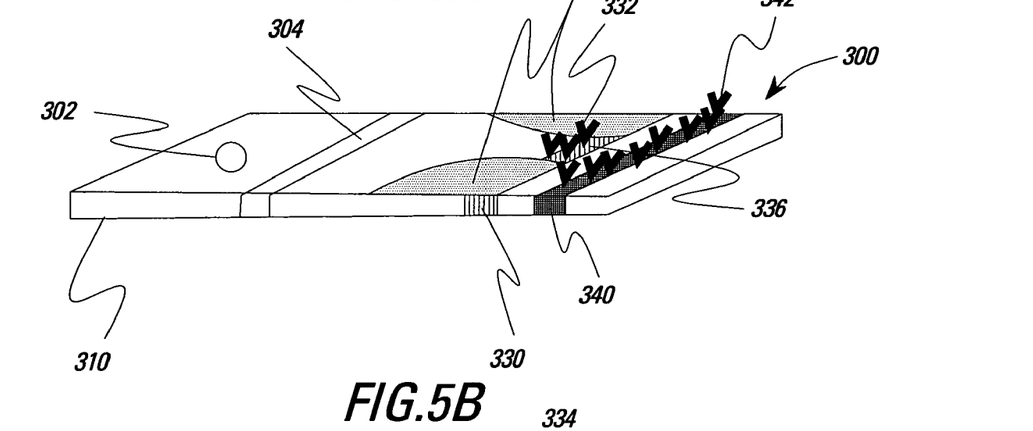
Figure 5C:
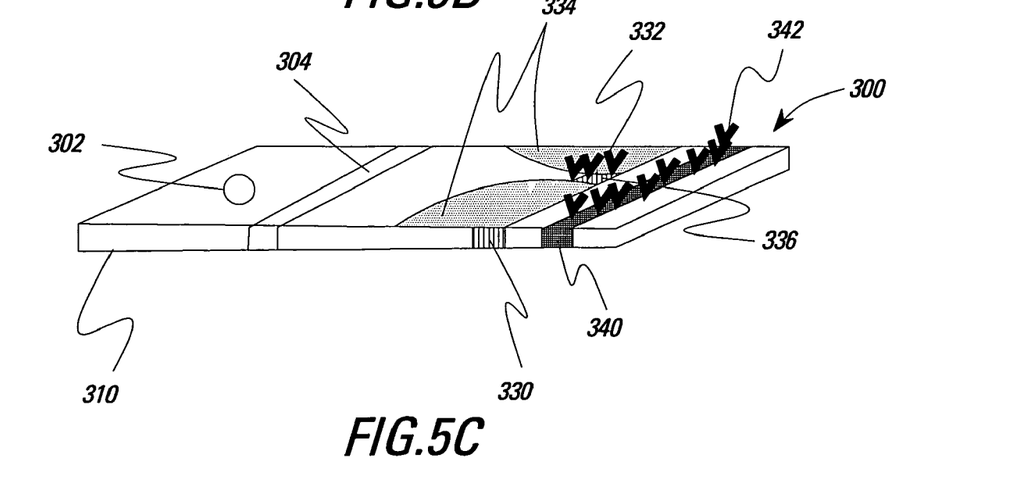

In another embodiment, a first region of the detection zone chemically differs from a second region of the detection zone. The first and the second region may vary in material, size, and shape in a predetermined manner. The lateral flow device is not limited by how the first and the second region chemically differ. In one embodiment, the first region of the detection zone may differ in hydrophobicity from a second region of the detection zone. For example, in a particular embodiment, the first region 334 of the detection zone has a surface (as illustrated in FIG. 5A-5C by the hatch marking) that is more hydrophobic than a second region, 336. In one embodiment, the first region 334 of the detection zone has a surface that is at least 20% more hydrophobic than the second region 336, as shown in FIG. 5A. In a particular embodiment, the first region 334 has a surface that is at least 50% more hydrophobic than the second region 336, as shown in FIG. 5B. In a more particular embodiment, the first region 334 has a surface that is at least 75% more hydrophobic than the second region 336, as shown in FIG. 5C. In other embodiments, the first region has a surface that is 20%-30%, 30%-40%, 40%-50%, 60%-70%, or 70%-80% more hydrophobic than the second region. The first region and the second region can be adjacent to each other or separated. Adjacent means with no space between the regions and the regions are in contact with each other. Separated means the regions are not in contact and separated by another region. The first region may extend beyond the detection zone, such as upflow from the detection zone, and be shaped in a manner to guide and concentrate the flow of the Raman-active complex to a desired portion of the detection zone. For example, as illustrated in FIG. 5A-5C, the first region begins upflow from the detection zone and extends to the detection zone and is shaped in a manner to guide and concentrate the flow of the Raman-active complex to a desired portion of the detection, such as the second region.

In a particular embodiment, a portion of the detection zone has a dimension that is less than another dimension of the lateral flow device upflow from the detection zone and a first region of the detection zone chemically differs from a second region of the detection zone.

The detection zone includes one or more immobilized target-binding moieties directed against a target of a Raman-active complex. In one embodiment, the immobilized target-binding moiety may attach to a Raman-active complex directly or via an intermediary or linker. Immobilized means at least partially immobilized such that the target-binding moiety at least partially attaches to the substrate. "Immobilized" may be used in combination with a term, and may include an insubstantial number or trace amount of movement while still being considered immobilized.

The detection zone may include a plurality of immobilized target-binding moieties directed against a target of a Raman-active complex. The lateral flow device is not limited by how the target-binding moieties are immobilized at the detection zone. Examples of immobilizing include, but are not restricted to, electrostatically, chemically, and physically adsorbing, either individually or in combination, wherein each of the plurality of target-binding moieties may be immobilized by different modes.

Furthermore, the plurality of immobilized target-binding moieties may be of the same or similar kind capable of attaching to the same type of targets, such that the detection zone can be capable of capturing a plurality of the same or similar kinds of targets. The plurality of immobilized target-binding moieties may also be of differing kind capable of attaching to different types of target, such that the detection zone can capture a plurality of different kinds of targets. Detection of the plurality of the targets is then based on the presence of Raman signal after removing any Raman-active tags that are unattached to a target from the test mixture.

A plurality of detection zones may be present, in which at least some may be partially co-located or spatially separated. The detection zone and the control zone may also be partially co-located or spatially separated.

Examples of the immobilized target-binding moieties include antibodies, aptamers, nucleic acids, selective ligands, and polypeptides, either individually or in any combination thereof. Examples of selective ligands include porphyrins, ethylenediaminetetraacetic acid (EDTA), and zinc fingers. Selective ligand means a ligand selective for a particular target or targets.

Other non-limiting examples of immobilized target-binding moieties include, but are not limited to, proteins, peptides, polypeptides, glycoproteins, lipoproteins, phospholipids, oligonucleotides, or the like, e.g. enzymes, immune modulators, receptor proteins, antibodies and antibody fragments, which preferentially bind marker substances that are produced by or associated with the target site.

Proteins are known that preferentially bind marker substances that are produced by or associated with lesions. For example, antibodies can be used against cancer-associated substances, as well as against any pathological lesion that shows an increased or unique antigenic marker, such as against substances associated with cardiovascular lesions, for example, vascular clots including thrombi and emboli, myocardial infarctions and other organ infarcts, and atherosclerotic plaques; inflammatory lesions; and infectious and parasitic agents.

Cancer states include carcinomas, melanomas, sarcomas, neuroblastomas, leukemias, lymphomas, gliomas, myelomas, and neural tumors. Infectious diseases include those caused by body invading microbes or parasites.

The protein substances useful as immobilized target-binding moieties include protein, peptide, polypeptide, glycoprotein, lipoprotein, or the like; e.g. hormones, lymphokines, growth factors, albumin, cytokines, enzymes, immune modulators, receptor proteins, antibodies and antibody fragments. The protein substances of particular interest are antibodies and antibody fragments. The terms "antibodies" and "antibody fragments" mean generally immunoglobulins or fragments thereof that specifically bind to antigens to form immune complexes.

The antibody may be a whole immunoglobulin of any class; e.g., IgG, IgM, IgA, IgD, IgE, chimeric or hybrid antibodies with dual or multiple antigen or epitope specificities. It can be a polyclonal antibody, particularly a humanized or an affinity-purified antibody from a human. It can be an antibody from an appropriate animal; e.g., a primate, goat, rabbit, mouse, or the like. If a paratope region is obtained from a non-human species, the target may be humanized to reduce immunogenicity of the non-human antibodies, for use in human diagnostic or therapeutic applications. Such a humanized antibody or fragment thereof is also termed "chimeric." For example, a chimeric antibody includes non-human (such as murine) variable regions and human constant regions. A chimeric antibody fragment can includes a variable binding sequence or complementarity-determining regions ("CDR") derived from a non-human antibody within a human variable region framework domain. Monoclonal antibodies are also suitable because of their high specificities. Useful antibody fragments include F(ab')$_2$, F(ab)$_2$, Fab', Fab, Fv, and the like including hybrid fragments. Particular fragments are Fab', F(ab')$_2$, Fab, and F(ab)$_2$. Also useful are any subfragments retaining the hypervariable, antigen-binding region of an immunoglobulin and having a size similar to or smaller than a Fab' fragment. An antibody fragment can include genetically engineered and/or recombinant proteins, whether single-chain or multiple-chain, which incorporate an antigen-binding site and otherwise function in vivo as immobilized target-binding moieties in substantially the same way as natural immunoglobulin fragments. The fragments may also be produced by genetic engineering.

Mixtures of antibodies and immunoglobulin classes can be used, as can hybrid antibodies. Multispecific, including bispecific and hybrid, antibodies and antibody fragments are sometimes desirable for detecting and treating lesions and includes at least two different substantially monospecific antibodies or antibody fragments, wherein at least two of the antibodies or antibody fragments specifically bind to at least two different antigens produced or associated with the targeted lesion or at least two different epitopes or molecules of a marker substance produced or associated with the targeted lesion. Multispecific antibodies and antibody fragments with dual specificities can be prepared analogously to anti-tumor marker hybrids.

Suitable MAbs have been developed against most of the microorganisms (bacteria, viruses, protozoa, other parasites) responsible for the majority of infections in humans, and many have been used previously for in vitro diagnostic purposes. These antibodies, and newer MAbs that can be generated by conventional methods, are also appropriate for use.

Proteins useful for detecting and/or treating cardiovascular lesions include fibrin-specific proteins; for example, fibrinogen, soluble fibrin, antifibrin antibodies and fragments, fragment $E_1$ (a 60 kDa fragment of human fibrin made by controlled plasmin digestion of crosslinked fibrin), plasmin (an enzyme in the blood responsible for the dissolution of fresh thrombi), plasminogen activators (e.g., urokinase, streptokinase and tissue plasminogen activator), heparin, and fibronectin (an adhesive plasma glycoprotein of 450 kDa) and platelet-directed proteins; for example, platelets, antiplatelet antibodies, and antibody fragments, anti-activated platelet antibodies, and anti-activated platelet factors.

In one embodiment, the immobilized target-binding moiety includes a MAb or a fragment thereof that recognizes and binds to a heptapeptide of the amino terminus of the β-chain of fibrin monomer. Fibrin monomers are produced when thrombin cleaves two pairs of small peptides from fibrinogen. Fibrin monomers spontaneously aggregate into an insoluble gel, which is further stabilized to produce blood clots.

The disclosure of various antigens or biomarkers that can be used to raise specific antibodies against them (and from which antibodies fragments may be prepared) serves only as examples, and is not to be construed in any way as a limitation of the invention.

Control Zone

The control zone includes one or more immobilized particle-binding moieties directed against and capable of attaching to a Raman-active tag. Immobilized means at least partially attached to the substrate. The lateral flow device is not limited by how the particle-binding moieties are immobilized at the control zone. Examples of immobilizing include, but are not restricted to, electrostatically, chemically, and physically adsorbing, either individually or in combination, wherein each of the plurality of particle-binding moieties may be immobilized by different modes. In one embodiment, the detection zone and the control zone are at least partially co-located or spatially separated along the flow path. Examples of the immobilized particle-binding moieties include, but are not limited to, antibodies, aptamers, nucleic acids, and polypeptides, either individually or in any combination thereof.

Another aspect of the invention includes a detection system. The detection system includes a lateral flow device and a Raman spectrometer capable of detecting a Raman-active complex, if present, at the detection zone. Examples of Raman spectrometers include dispersive grating, interferometer, and tunable filters, employing single or multiple detectors, and with varying light sources, such as laser, light emitting diode, and white light. Examples of single channel detectors include photo multiplier tube and avalanched photodiode. Examples of multiple channel detectors include charged couple device. In one embodiment, the lateral flow device is as described above and is positioned within a Raman spectrometer capable of detecting Raman-active complexes in the detection zone. In another embodiment, the lateral flow device further includes a control zone and is positioned within a Raman spectrometer capable of detecting a Raman-active tag in the control zone.

The lateral flow device may be used to detect the presence of various target organisms or molecules, which may be dangerous or toxic, such as anthrax. Raman spectrometer detection system may generate information rich data. The vibrational data provides a spectral 'fingerprint'. Damage to sample may be minimized. The samples can be analyzed relatively non-invasively, such as inside bottles and bags. Many samples can be analyzed 'as is' with minimal or no sample preparation. The analysis is relatively rapid; some samples may be analyzed in less than 60 seconds. Samples in differing forms may be analyzed, such as crystals, powders, and liquids with little or no reconfiguration of the detection system. Remote sensing may also be possible and is suited for fiber optic probes.

Figure 6:
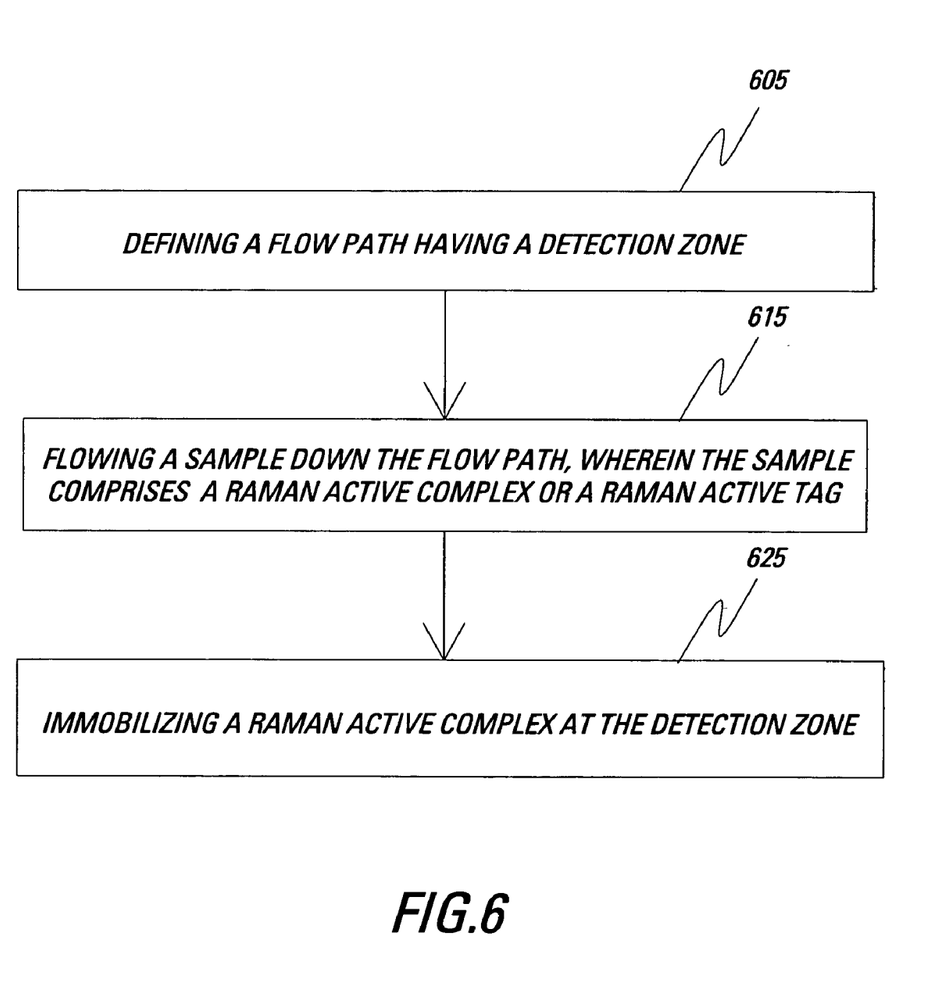
FIG. 6 is flow chart of a method of detecting the presence of a target in a sample in accordance with an embodiment of the invention.

With reference to FIG. 6, a method of conducting a lateral flow assay is described. Lateral flow assays and devices include, but are not limited to, immunochromatographic assays and strip-based immunoassays. The method, at Step 605, includes defining a flow path having a detection zone. In a particular embodiment, the flow path has a control zone downflow from the detection zone. Step 615 includes flowing a sample down the flow path. In one embodiment, the sample is deposited on the sample zone. The sample includes a Raman-active complex or a Raman-active tag. Step 625 includes immobilizing a Raman-active complex, if present, at the detection zone. In a particular embodiment, a Raman-active tag is also immobilized at the control zone. In one embodiment, a portion of the detection zone has a dimension that is less than another dimension of the lateral flow device upflow from the detection zone and or a first region of the detection zone has a chemical difference from a second region of the detection zone as described above.

In one embodiment, the sample is placed in a sample zone and is drawn through a contact zone containing immuno-SERS particles against the target pathogen tags (i.e. the Raman-active tags). The immuno-SERS particles against the target pathogen tags (i.e. the Raman-active tags) attach to the directed target to form Raman-active complexes. Immobilized target-binding moieties (i.e. immobilized pathogen-specific antibodies) in the detection zone bind the immuno- SERS-pathogen complexes. In one embodiment, the immobilized binding moieties on the detection zone or the control zone are provided by a conjugate pad. Immuno-SERS particles captured in a control zone are used as a positive control for reagent flow and SERS detection.

In one embodiment, the lateral flow assay further includes generating a Raman spectrum of the Raman-active complex from the detection zone. After a given time interval, the Raman spectrum may be taken. The Raman spectrum may be correlated to the presence of a target attached to the Raman-active complex. Furthermore, the Raman spectrum may be correlated to the identification and or quantification of the target attached to the Raman-active complex.

The sample may include a plurality of targets and the method of conducting the lateral flow assay includes being able to detect a plurality of targets, sequentially or simultaneously. Thus, in one embodiment, the sample includes a plurality of Raman-active complexes attached to a plurality of targets. The method further includes generating a plurality of Raman spectrums, wherein the plurality of Raman spectrums correlate to the presence or identification of targets that are different from each other. Detection, identification, and or quantification of the plurality of the targets is then based on correlating the plurality of Raman signals to the plurality of targets in the sample.

The method is not limited by how the Raman-active tag, target, or Raman-active complex are provided. In one embodiment, the Raman-active tags unattached to a target and Raman-active complex are simultaneously provided. In another embodiment, the Raman-active tags unattached to a target and Raman-active complex are sequentially provided. In one embodiment, the Raman-active complex is formed by providing a target and Raman-active tag, so that the Raman-active complex is formed subsequently.

In one embodiment, immobilizing the Raman-active complex at the detection zone includes providing a detection zone having an immobilized target-binding moiety capable of attaching to the target of the Raman-active complex. Immobilizing the Raman-active tag at the control zone includes providing a control zone having an immobilized particle-binding moiety capable of attaching one or more Raman-active tags. The method is not limited by how the Raman-active complex, Raman-active tags, and targets are immobilized at the detection and control zone. The method is also not limited by how the Raman-active complex, Raman-active tags, and targets attach. Examples of attaching include, but are not restricted to, electrostatically, chemically, and physically.

Another method of conducting a lateral flow assay includes concentrating a Raman-active complex, if present, in a detection zone of a lateral flow assay. In one embodiment, concentrating includes more Raman-active complexes in one portion of the detection zone compared to another portion of the detection zone. In a particular embodiment, concentrating Raman-active complex includes a portion of the detection zone having at least 20% more Raman-active complex than another portion. In a particular embodiment, concentrating Raman-active complex includes a portion of the detection zone having at least 50% more Raman-active complex than another portion. In another particular embodiment, concentrating Raman-active complex includes a portion of the detection zone having at least 75% more Raman-active complex than another portion.

In one embodiment, the Raman-active complex is concentrated at a portion of the detection zone that has a dimension that is less than another dimension of the lateral flow device upflow from the detection zone. In a particular embodiment, the Raman-active complex is concentrated at a portion of the detection zone that has a dimension at least 20% less than another dimension of the lateral flow device upflow from the detection zone. In a more particular embodiment, the Raman-active complex is concentrated at a portion of the detection zone that has a dimension at least 50% less than the another dimension of the lateral flow device upflow from the detection zone. In another embodiment, the Raman-active complex is concentrated at a portion of the detection zone that has a dimension at least 75% less than another dimension of the lateral flow device upflow from the detection zone. In one embodiment, the dimension includes width.

In one embodiment, the Raman-active complex is concentrated at the portion of the detection zone by chemically differing from another portion of the detection zone by having a surface that is at least 20% more hydrophilic than another portion of the detection zone. In a particular embodiment, the Raman-active complex is concentrated at the portion of the detection zone that has a surface that is at least 50% more hydrophilic than another portion of the detection zone.

In one embodiment, the Raman-active complex is concentrated at a second region of the detection zone that chemically differs from a first region of the detection zone. The first region of the detection zone may differ in hydrophobicity from the second region. For example, in an embodiment, the Raman-active complex is concentrated at the second region 336, as opposed to the first region 334, by having a first region 334 with a surface (as illustrated in FIG. 5A-5C by the dotted hatch marking) that is more hydrophobic than the second region, 336. In a particular embodiment, the Raman-active complex is concentrated at the second region 336, as opposed to the first region 334, by having a first region 334 with a surface that is at least 20% more hydrophobic than the second region 336, as shown in FIG. 5A. In a more particular embodiment, the Raman-active complex is concentrated at the second region 336, as opposed to the first region 334, by having a first region 334 with a surface that is at least 50% more hydrophobic than the second region 336, as shown in FIG. 5B. In yet a more particular embodiment, the Raman-active complex is concentrated at the second region 336, as opposed to the first region 334, by having a first region 334 with a surface that is at least 75% more hydrophobic than the second region 336, as shown in FIG. 5C. In other embodiments, the first region has a surface that is 20%-30%, 30%-40%, 40%-50%, 60%-70%, or 70%-80% more hydrophobic than the second region.

In one embodiment, Raman-active complex is concentrated at the portion of the detection zone by one or more barriers. The barrier may be positioned in or around the detection zone to guide the flow of the Raman active complex to the desired portion of the detection zone. For example, in one embodiment, one or more barriers may be position in the detection zone to minimize or prevent access to another or other portions of the detection zone. The barriers may be erected or placed around the other portions of the detection zone, such as like a fence, to minimize or prevent access such that the Raman active complex will flow to the desired portion of the detection zone. The barrier may be of a predetermined shape, size, and material based on intended use. The barrier may include, but is not limited to, wood, ceramic, metal, or plastic, either individually or in a combination of two or more.

Also disclosed is a method of making a lateral flow device. The method includes providing a lateral flow device with a detection zone. A portion of the detection zone has a dimension that is less than another dimension of the lateral flow device upflow from the detection zone and or a first region of the detection zone has a chemical difference from a second region of the detection zone.

The method is not limited by when the first and second regions with the chemical difference are provided or when the differing dimensions are created. For example, in one embodiment, the first and second are simultaneously provided. In another embodiment, the first and second regions are sequentially provided.

The method is also not limited by how the first and second regions with the chemical difference are provided or how the differing dimensions are created. For example, in one embodiment, providing a portion of the detection zone with a dimension less than another dimension of the lateral flow device upflow from the detection zone includes removing a section of detection zone or putting a barricade to direct flow towards a portion of detection zone. A section of the detection zone may be removed in various ways, such as, but not limited to, cutting, scraping, a scalpel, razor, and the like. A first region of the detection zone may be provided with a chemical difference from a second region of the detection zone, such as but not limited to, by coating, illuminating the detection zone with light, or locally heating, or a combination thereof.

In one embodiment, the first region is chemically different from the second region in hydrophobicity. The difference in the degree of hydrophobicity between the first and the second regions may be created by the material of the coating and or number of coatings as well as by coating the first and or the second region. In one embodiment, the difference in hydrophobicity is provided by disposing one or more hydrophobic coatings to the first region (i.e. portion) of the detection zone. Furthermore, a plurality of hydrophobic coatings may be provided to the first region to make the surface of the first region at least 20% more hydrophobic than the second region. In another embodiment, the difference in hydrophobicity is provided by disposing one or more hydrophilic coatings to the second region of the detection zone. Furthermore, a plurality of hydrophilic coatings may be provided to the second region to make the surface of the second region at least 20% more hydrophilic than the second region. In other embodiments, the second region has a surface that is 20%-30%, 30%-40%, 40%-50%, 60%-70%, or 70%-80% more hydrophilic than the first region. Furthermore, the first region may be provided with one or more hydrophobic coatings while the second region is provided with one or more hydrophilic coatings.

The following examples illustrate some features of the invention and are not intended to limit the invention thereto. Particularly, the examples demonstrate that it is possible to use immuno-functionalized Raman-active tags to detect the presence of a specific target organism in a lateral flow assay. In these experiments, a Raman signal was only detected at the detection zone when the appropriate Raman-active complex attached to a target and a target-binding moiety immuno-functionalized for that specific target organism attached to the Raman-active complex were both present. Furthermore, the experiments were conducted to determine whether narrowing the width of the detection zone increases the amount of signal generated. Narrowing the width concentrates more of the SERS tags attached to a target (i.e. Raman-active complex) to a smaller area, thereby increasing the signal strength at that location.

The detection of targets with Raman-active analytes are summarized in Table 1. The two targets are *Bacillus anthracis* (sterne), and *Clostridium botulinum* toxoid and the analytes are Quinoline thiol (QSH) and BPE.

TABLE 1

Lateral flow devices using SERS nanoparticle tags to detect targets

| Example | SERS Tag | Target | Detection zone |
|---|---|---|---|
| 1A | QSH | *Bacillus anthracis* (sterne) | untapered |
| 1B | QSH | *Bacillus anthracis* (sterne) | tapered |
| 2A | Trans-bis(pyridyl)ethylene (BPE) | *Clostridium botulinum* toxoid | untapered |
| 2B | Trans-bis(pyridyl)ethylene (BPE) | *Clostridium botulinum* toxoid | tapered |

EXAMPLE 1B AND 1B

SERS-Based Detection of Anthrax Using Untapered and Tapered Lateral-Flow Device

Reagents used were anthrax spores and Raman-active tags. The Raman-active tags were SERS-active nanoparticles directly attached to anti-anthrax antibodies. The Raman-active analyte was QSH. Anti Anthrax test kits (commercially available from Tetracore, Inc., Rockville, Md. (lot # 501130)) after removing the conjugate pad and replacing with SERS particles were used. Sonicated Anthrax Vaccine strain ($1.3 \times 10^9$/ml) and standard buffer were used (both commercially available from Tetracore, Inc.).

Method:

An amount of 1 μL of Anthrax spores were diluted 1/100 with buffer (final concentration $1.3 \times 10^4$ per μL). The diluted Anthrax spore solution was mixed with 25 μL of anti anthrax SERS-active tags and 125 μL of buffer to give ($1.3 \times 10^5$ or $1.3 \times 10^6$ cells/test). The mixture was incubated at room temperature for several minutes. A portion of the mixture was deposited onto an untapered lateral flow device (Example 1A) and a tapered lateral flow device (Example 1B). Lateral flow device 2 (Example 1B) had the width of the detection zone tapered or narrowed by about 70% compared to the width upflow from the detection zone.

The two lateral flow devices were analyzed for SERS signal and the signal intensities at the detection zones were compared.

Intensity of the tapered or narrower detection zone compared to the untapered detection zone was determined by the visible darkness of a line where the Raman-active complexes are collected. The darkness of the lines is proportional to the concentration of the Raman-active complexes. At $1.3 \times 10^5$ cells/test, the line was much darker for the tapered detection zone (Example 1B) than the untapered detection zone (Example 1A).

Thus, Example 1 demonstrates how it is possible to use immuno-functionalized Raman-active tags in a tapered lateral flow assay to detect the presence of a specific target organism. Example 1 also demonstrates how it is possible to modify a detection zone to increase the signal and thereby improve detection of immuno-functionalized Raman-active tags. In these experiments, a significant Raman signal is only detected when the appropriate target organism and Raman-active tags immuno-functionalized for that specific target organism to detect the presence of that specific target organism are both present.

EXAMPLE 2

SERS-Based Detection of Botulinum Toxoid Using Untapered an Tapered Lateral-Flow Device Reagents used were Botulinum toxoid solution and Raman-active tags. The Raman-active tags were SERS-active nanoparticles (Raman-active) directly attached to anti-botoxoid antibodies and BPE was the Raman-active analyte. Anti botox test kits (commercially available from Tetracore, Inc. Rockville, Md. (lot # 501130)) were used after removing the conjugate pad and replacing with SERS particles. Botulinum Toxoid complex A (1 mg/mL stock) and standard buffer were used (both commercially available from Tetracore, Inc.).

Method:

Botulinum Toxoid complex A was diluted 1/1000 (to 1 ng/μL) using standard buffer. An amount of 60 μL of the diluted botoxoid A complex (60 ng total, 30 per lateral flow device strip) was mixed with 50 μL of anti toxoid SERS tags. The mixture was incubated at room temperature for several minutes and 190 μL of standard buffer was added. A portion of the mixture (i.e. sample) was deposited onto the untapered lateral flow device 1 (Example 2A) and the tapered lateral flow device 2 (Example 2B).

Lateral flow device 1 (Example 2A) was the control where the detection zone was not chemically or physically tapered.

Lateral flow device 2 (Example 2B) had the width of the detection zone tapered or narrowed by about 70% compared to the width upflow from the detection zone.

After depositing the sample, the lateral flow devices were incubated for 15 min.

The two lateral flow devices were analyzed for SERS signal and the signal intensities at the detection zones were compared.

Visual: Both lateral flow devices produced a dark testline indicative of botoxoid detection. However, the line at the tapered detection zone (lateral flow device 2) appeared darker than the untapered lateral flow device 1. As with the anthrax detection, tapering the detection zone did not affect the signal of the control zone, which is intense throughout its full width.

Figure 7:
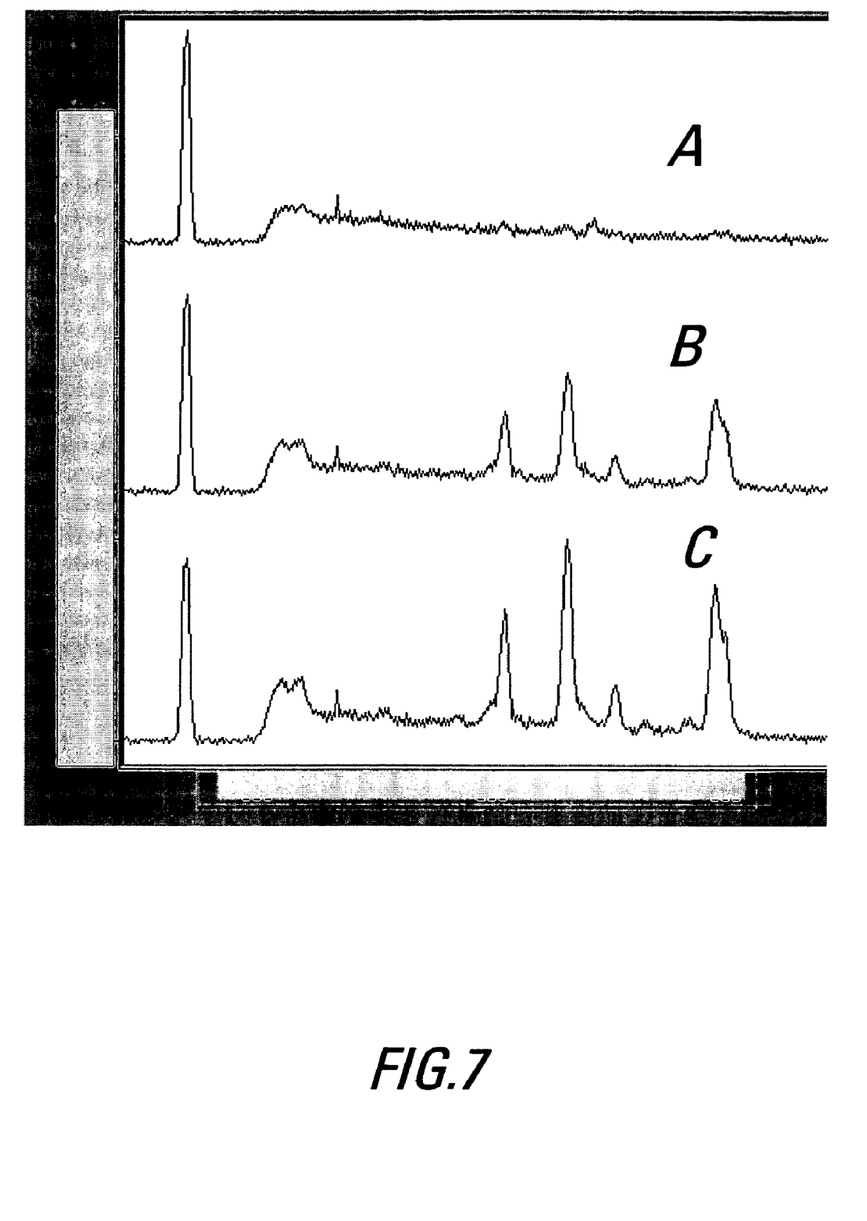

SERS: SERS collected for 3 sec at 10% laser. The SERS signal from the tapered lateral flow device had higher signal compared to the untapered lateral flow device, as shown in FIG. 7A-7C and described below. For FIG. 7A-7C, the x-axis is wavelength in nm and the y-axis indicates the intensity of the SERS signal and begins at a 0 reference for each graph in FIG. 7A-7C.

FIG. 7A is background SERS spectrum signal obtained from the tapered lateral flow assay between the detection zone and the control zone of the tapered or in the presence of 30 ng botoxoid. There was a small amount of Raman signal due to non-specific binding of the Raman-active tag to the substrate.

FIG. 7B is a SERS spectrum obtained from the untapered detection zone of the lateral flow assay in the presence of 30 ng of the target molecule botulinum toxoid. The Raman-active tags immuno-functionalized with anti-botulinum toxin antibodies (target-binding moiety) attached to the target botulinum toxin and formed Raman-active complex. The detection zone had immobilized anti-botulinum toxin antibodies (immobilized target-binding moiety) which then retained the Raman-active complex at the detection zone. Consequently, there was a detectable Raman signal from the material collected from the detection zone which was greater than the background. Specifically, the ratio of test line to baseline intensity for the peak at 865 nm was 7.1 for the untapered detection zone.

FIG. 7C is a SERS spectrum obtained from the tapered detection zone of lateral flow assay in the presence of 30 ng of target molecule botulinum toxoid. Consequently, there was a detectable Raman signal from the material collected from the detection zone, which was greater than the background and the untapered detection zone. Specifically, the ratio of test line to baseline intensity for the peak at 865 nm was 11.95 for the tapered detection zone. Hence, the tapered detection zone gave a better signal to noise ratio by 68% compared to the untapered detection zone, which is the ratio of 7.1 (from FIG. 7B) to 11.95 (from FIG. 7C).

Thus, Example 2 demonstrates how it is possible to use immuno-functionalized Raman-active tags in a tapered lateral flow assay to detect the presence of another specific target organism. Example 2 also demonstrates how it is possible to modify a detection zone to increase the visual signal at the detection zone and SERS signal and thereby improve detection of immuno-functionalized Raman-active tags. In these experiments, a significant Raman signal is only detected when the appropriate target organism and Raman-active tags immuno-functionalized for that specific target organism to detect the presence of that specific target organism are both present.

While the invention has been described in detail in connection with only a limited number of aspects, it should be understood that the invention is not limited to such disclosed aspects. Rather, the invention can be modified to incorporate any number of variations, alterations, substitutions or equivalent arrangements not heretofore described, but which are commensurate with the scope of the claims. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A lateral flow device comprising:
   a substrate having a flow path; and
   a detection zone disposed along the flow path, wherein the detection zone comprises an immobilized target-binding moiety directed against a target of a Raman-active complex; and
   wherein a first region of the detection zone has a chemical difference from a second region of the detection zone by having a surface that is at least 20% more hydrophobic than the second region.

2. The lateral flow device of claim 1, wherein the target comprises at least one target selected from a group consisting of prokaryotic cells, eukaryotic cells, viruses, bacteria, proteins, polypeptides, toxins, liposomes, nucleic acids, and beads.

3. The lateral flow device of claim 1, wherein the immobilized target-binding moiety comprises at least one moiety selected from a group consisting of antibodies, aptamers, nucleic acids, selective ligands, and polypeptides.

4. The lateral flow device of claim 1, wherein the detection zone comprises a plurality of immobilized target-binding moieties.

5. The lateral flow device of claim 4, wherein the plurality of immobilized target-binding moieties are directed against targets different from each other.

6. The lateral flow device of claim 1, wherein a portion of the detection zone has a dimension that is less than another dimension of the lateral flow device upflow from the detection zone and has a dimension that is less than another dimension of the lateral flow device downflow from the detection zone.

7. The lateral flow device of claim 1, further comprising a control zone disposed along the flow path downflow from the detection zone, wherein the control zone comprises an immobilized particle-binding-moiety directed against a Raman-active tag.

8. The lateral flow device of claim 7, wherein the detection zone and control zone are at least partially spatially co-located.

9. The lateral flow device of claim 1, wherein a portion of the detection zone has a dimension that is less than another dimension of the lateral flow device upflow from the detection zone and wherein the first region of the detection zone has a chemical difference from a second region of the detection zone.

10. The lateral flow device of claim 9, wherein the dimension of the detection zone is at least 20% less than the another dimension of the lateral flow device upflow from the detection zone.

11. The lateral flow device of claim 10, wherein the dimension of the detection zone is at least 50% less than the another dimension of the lateral flow device upflow from the detection zone.

12. The lateral flow device of claim 11, wherein the dimension of the detection zone is at least 75% less than the another dimension of the lateral flow device upflow from the detection zone.

13. The lateral flow device of claim 9, wherein the dimension of the detection zone comprises width.

14. The lateral flow device of claim 11, wherein the first region has a surface that is at least 50% more hydrophobic than the second region.

15. The lateral flow device of claim 14, wherein the first region has a surface that is at least 75% more hydrophobic than the second region.

16. A detection system comprising:
a lateral flow device comprising:
   a substrate having a flow path; and
   a detection zone disposed along the flow path, wherein the detection zone comprises an immobilized target-binding moiety directed against a target of a Raman-active complex;
      wherein a first region of the detection zone has a chemical difference from a second region of the detection zone by having a surface that is at least 20% more hydrophobic than the second region, and
a Raman spectrometer capable of detecting a Raman-active complex at the detection zone.

17. The detection system of claim 16, wherein the portion of the detection zone has a dimension that is less than another dimension of the lateral flow device upflow from the detection zone.

18. The detection system of claim 16, wherein the dimension of the detection zone is at least 20% less than the another dimension of the lateral flow device upflow from the detection zone.

19. A method of conducting a lateral flow assay comprising:
i) defining a flow path having a detection zone, wherein a first region of the detection zone has a chemical difference from a second region of the detection zone by having a surface that is at least 20% more hydrophobic than the second region;
ii) flowing a sample down the flow path, wherein the sample comprises a Raman-active complex or a Raman-active tag; and
iii) immobilizing a Raman-active complex, if present, at the detection zone.

20. The method of claim 19, wherein immobilizing the Raman-active complex comprises immobilizing the Raman-active complex at a portion of the detection zone that has a dimension that is less than another dimension of the lateral flow device upflow from the detection zone.

21. The method of claim 20, wherein the dimension of the detection zone is at least 20% less than the another dimension of the lateral flow device upflow from the detection zone.

22. The method of claim 21, wherein the dimension of the detection zone is at least 50% less than the another dimension of the lateral flow device upflow from the detection zone.

23. The method of claim 22, wherein the dimension of the detection zone is at least 75% less than the another dimension of the lateral flow device upflow from the detection zone.

24. The method of claim 20, wherein the dimension comprises width.

25. The method of claim 19, wherein immobilizing the Raman-active complex comprises immobilizing the Raman-active complex at the second region of the detection zone that chemical differs from the first region of the detection zone.

26. The method of claim 19, wherein the first region has a surface that is at least 50% more hydrophobic than the second region.

27. The method of claim 26, wherein the first region has a surface that is at least 75% more hydrophobic than the second region.

28. The method of claim 19, further comprising generating a Raman spectrum of the Raman-active complex from the detection zone.

29. The method of claim 28, further comprising correlating the generated Raman spectrum to a presence of a target.

30. The method of claim 28, further comprising correlating the generated Raman spectrum to an identification of the target.

31. The method of claim 28, further comprising correlating the generated Raman spectrum to a quantity of the target.

32. The method of claim 19, wherein the sample comprises a plurality of Raman-active complexes attached to a plurality of targets different from each other.

33. The method of claim 32, further comprising generating a plurality of Raman spectrums, wherein the plurality of Raman spectrums correlate to the presence of the plurality of targets different from each other.

34. The method of claim 33, further comprising correlating the plurality of generated Raman spectrums to an identification of the plurality of targets different from each other.

35. The method of claim 33, further comprising correlating the plurality of generated Raman spectrums to a quantification of the plurality of targets different from each other.

36. The method of claim 19, wherein flowing the sample comprising providing the Raman-active tags unattached to a target and Raman-active complex simultaneously.

37. The method of claim 19, wherein flowing the sample comprising providing the Raman-active tags unattached to a target and Raman-active complex sequentially.

38. The method of claim 19, wherein the Raman-active complex is provided by a target and Raman-active particle.

39. The method of claim 19, wherein immobilizing the Raman-active complex at the detection zone comprises providing a detection zone having an immobilized target-binding moiety capable of attaching to the target of the Raman-active complex.

40. The method of claim 19, further comprising a control zone downflow from the detection zone and immobilizing a Raman-active tag at the control zone.

41. The method of claim 40, wherein immobilizing the Raman-active tag at the control zone comprises providing a control zone having an immobilized particle-binding moiety capable of attaching to the Raman-active tag.

42. A method of conducting a lateral flow assay comprising:
concentrating a Raman-active complex at a portion of a detection zone of a lateral flow assay, wherein the portion of the detection zone has a surface that is at least 20% more hydrophilic than another portion of the detection zone.

43. The method of claim 42, wherein the Raman-active complex is concentrated at the portion of the detection zone that has a dimension that is less than another dimension of the lateral flow device upflow from the detection zone.

44. The method of claim 43, wherein the portion of the detection zone has a dimension that is at least 20% less than the another dimension of the lateral flow device upflow from the detection zone.

45. The method of claim 44, wherein the dimension of the detection zone is at least 50% less than the another dimension of the lateral flow device upflow from the detection zone.

46. The method of claim 42, wherein the Raman-active complex is concentrated at the portion of the detection zone by a barrier against another portion of the detection.

47. The method of claim 46, wherein the barrier comprises a plurality of barriers against another portion of the detection zone.

48. The method of claim 42, wherein the portion of the detection zone has a surface that is at least 50% more hydrophilic than the another portion of the detection zone.

49. A method of making a lateral flow device comprising:
(i) providing a lateral flow device with a detection zone, wherein a first region of the detection zone has a chemical difference from a second region of the detection zone by having a surface that is at least 20% more hydrophobic than the second region.

50. The method of claim 49, comprising providing a portion of the detection zone with a dimension that is less than another dimension of the lateral flow device upflow from the detection zone.

51. The method of claim 50, comprising providing the portion of the detection zone with a dimension that is less than another dimension of the lateral flow device downflow from the detection zone.

52. The method of claim 49, wherein said providing the first region of the detection zone the chemical difference from the second region of the detection zone comprises treating with at least one member selected from a group consisting of coating, heating, and UV treatment.

53. The method of claim 50, wherein said providing a portion of the detection zone with a dimension that is less than another dimension of the lateral flow device comprises removing a portion of the detection zone.

\* \* \* \* \*